US006800790B2

(12) United States Patent
Spradling et al.

(10) Patent No.: US 6,800,790 B2
(45) Date of Patent: *Oct. 5, 2004

(54) METHOD FOR MAINTENANCE AND PROPAGATION OF GERMLINE STEM CELLS USING MEMBERS OF THE TFG-β FAMILY OF GROWTH FACTORS

(75) Inventors: Allan C. Spradling, Baltimore, MD (US); Ting Xie, Baltimore, MD (US)

(73) Assignee: Carnegie Institution of Washington, Washington, DC (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/358,937

(22) Filed: Jul. 23, 1999

(65) Prior Publication Data

US 2002/0168694 A1 Nov. 14, 2002

Related U.S. Application Data

(60) Provisional application No. 60/094,008, filed on Jul. 24, 1998.

(51) Int. Cl.⁷ .................. C12P 21/00; A01K 67/00; C12N 5/06; C12N 5/00; A01N 63/00
(52) U.S. Cl. .................. 800/4; 800/13; 800/21; 435/325; 435/348; 435/440; 424/93.1
(58) Field of Search .................. 435/7.21, 70.1, 435/325, 455, 348; 424/93.1; 800/3, 4, 13, 21; 514/44

(56) References Cited

U.S. PATENT DOCUMENTS

| | | |
|---|---|---|
| 5,166,190 A | 11/1992 | Mather et al. |
| 5,216,126 A | 6/1993 | Cox et al. |
| 5,286,654 A | 2/1994 | Cox et al. |
| 5,453,357 A | 9/1995 | Hogan |
| 5,484,768 A | 1/1996 | Donahue et al. |
| 5,547,854 A | 8/1996 | Donahoe et al. |
| 5,563,059 A | 10/1996 | Alak et al. |
| 5,650,276 A | 7/1997 | Smart et al. |
| 5,661,126 A | 8/1997 | Donahoe et al. |
| 5,670,372 A | 9/1997 | Hogan |
| 5,683,906 A | 11/1997 | Moore |
| 5,690,926 A | 11/1997 | Hogan |
| 5,693,534 A | 12/1997 | Alak et al. |
| 5,736,396 A | 4/1998 | Bruder et al. |
| 5,750,376 A | 5/1998 | Weiss et al. |
| 5,753,506 A | 5/1998 | Johe |
| 5,756,457 A | 5/1998 | Wang et al. |
| 5,807,708 A | 9/1998 | Falb et al. |
| 5,817,453 A | 10/1998 | Brinster |
| 5,830,682 A | 11/1998 | Moore |
| 5,837,538 A | 11/1998 | Scott et al. |
| 5,851,832 A | 12/1998 | Weiss et al. |
| 5,854,207 A | 12/1998 | Lee et al. |
| 5,858,354 A | 1/1999 | Brinster |
| 5,908,784 A | 6/1999 | Johnstone et al. |
| 5,912,224 A | 6/1999 | Donahoe et al. |
| 5,916,870 A | 6/1999 | Lee et al. |

OTHER PUBLICATIONS

Lin et al., Germline Stem Cell Division and Egg Chamber Development in Transplanted Drosophila Germaria, 1993; Developmental Biology 159:140–152.*
Twombly et al., The TGF–B skignaling pathway is essential for *Drosophila oogensis*, 1996, Development 122: 1555–1565.*
Mullins et al. "Perspective Series . . . " Journal of Clincal Investigations 97:1557–1560 (Apr. 1996).
Wall et al. "Transgenic Dairy Cattle . . . " Journal of Dairy Science 80:2213–2224 (1997).
Hammer et al. "Genetic engineering . . . " Journal of animal science 63:269–278 (Jul. 1986).
McPherron et al. "Doubling muscling . . . " PNAS 94:12457–12461 (Nov. 1997).
Forbes et al., The Role Segment Polarity Genes During Early Oogenesis in Drosophila, Development 122, 1996, pp. 3283–3294.
Xie et al., Decapentaplegic is Essential for the Maintenance and Division of Germline Stem Cells in the Drosophila ovary, Cell. vol. 94, 1998, pp. 251–260.
Hogan, Bone Morphogenetic Proteins: Multifunctional Regulators of Vertebrate Development, Genes & Development 10, 1996, pp. 1580–1594.
Massague, TGFB Signaling: Receptors, Transducers, and Mad Proteins, Cell. vol. 85, 1996, pp. 947–950.
The FlyBase Consortium, "The FlyBase database of the Drosophila genome projects and community literature," Nucl. Acids. Res., 1999, 27:85–88.
Haifan Lin and Allan C. Spradling, "Germline Stem Cell Division and Egg Chamber Development in Transplanted *Drosophila* Germaria," Developmental Biology 159, 1993, pp. 140–152.
Haifan Lin and Allan C. Spradling, "A Novel Group of Pumlio Mutations Affects the Asymmetric Division of Germline Stem Cells in the *Drosophila* Ovary," Development 124, 1997, pp. 2463–2476.
Jonathan Margolis and Allan Spradling, "Identification and Behavior of Epithelial Stem Cells in the *Drosophila* Ovary," Development 121, 1995, pp. 3797–3807.

(List continued on next page.)

*Primary Examiner*—Deborah J. Reynolds
*Assistant Examiner*—Joseph Woitach
(74) *Attorney, Agent, or Firm*—Morgan, Lewis & Bockius LLP

(57) ABSTRACT

The TGF-β family of growth factors, particularly the bone morphogenetic protein (BMP)-2/4 homolog decapentaplegic (dpp), are specifically required to maintain germline stem cells and promote their division. Overexpression of dpp blocks germline stem cell differentiation. Mutations in dpp or its receptor saxophone accelerate stem cell loss and retard stem cell division. dpp signaling is directly received by germline stem cells, and thus dpp signaling helps define a niche that controls germline stem cell proliferation.

13 Claims, No Drawings

OTHER PUBLICATIONS

Erika Matunis, John Tran, Pierre Gonczy, Kim Caldwell and Stephen Dinardo, "*Punt* and *Schnurri* Regulate a Somatically Derived Signal that Restricts Proliferation of Committed Progenitors in the Germline," Development 124, 1997, pp. 4383–4391.

A.C. Spradling, M. De Cuevas, D. Drummond–Barbosa, L. Keyes, M. Lilly, M. Pepling, and T. Xie, "The *Drosophila* Germarium: Stem Cells, Germ Line Cysts, and Oocytes," Cold Spring Harbor Symposia on Quantitative Biology, vol. LXII, 1997, pp. 25–34.

Vern Twombly, Ronald K. Blackman, Hui Jin, Jonathan M. Graff, Richard W. Padgett and William M. Gelbart, "The TGF–β Signaling Pathway is Essential for *Drosophila* Oogenesis," Development 122, 1996, pp. 1555–1565.

Ting Xie and Allan C. Spradling, "*Decapentaplegic* Is Essential for the Maintenance and Division of Germline Stem Cells in the *Drosophila* Ovary," Cell, vol. 94, Jul. 24, 1998, pp. 251–260.

* cited by examiner

METHOD FOR MAINTENANCE AND PROPAGATION OF GERMLINE STEM CELLS USING MEMBERS OF THE TFG-β FAMILY OF GROWTH FACTORS

RELATED APPLICATIONS

This application claims priority from provisional U.S. Application Ser. No. 60/094,008, filed Jul. 24, 1998.

BACKGROUND OF THE INVENTION

1. Field of the Invention

This invention relates to members of the transforming growth factory-β family and their regulation of cell division, cell survival, and the specification of cell fates. Particularly, the invention relates to the bone morphogenetic protein (BMP)-2/4 homolog decapentaplegic (dpp) and its role in the maintenance of stem cells. For example, a dpp-based method for maintenance and controlling the division of germline stem cells, and a dpp-based method for defining a niche that controls germline stem cell proliferation are disclosed. Additionally, the invention provides a model of ovarian tumor development. The invention further relates to a dpp-based method for propagating stem cells in an undifferentiated state in vivo or by culturing in vitro.

2. Description of Related Art

In many adult tissues that undergo continuous cell turnover, a population of stem cells is responsible for replacing lost cells. Because of their pivotal role in controlling growth and neoplasia, the mechanisms regulating stem cell function are of great interest (reviewed by Potter and Loeffler, 1990; Doe and Spana, 1995; Lin, 1997; Morrison et al., 1997). Two mechanisms have been proposed to maintain stem cell divisions and regulate the differentiation of stem cell daughters: intrinsic factors and extracellular signals. Asymmetrically localized intrinsic factors help specify the fates of neuroblast daughters in Drosophila embryos (Doe and: Spana, 1995). Extracellular signals from surrounding cells mediated by cell surface-associated ligands and diffusible factors are frequently involved (Potter and Loeffler, 1990; Morrison et al., 1997). The identification of several of these factors has made it possible to culture some types of stem cell in vitro.

The Drosophila ovary presents an excellent system for studying two distinct groups of stem cells that remain active during much of adult life (reviewed by Spradling et al., 1997). The adult ovary contains 14–16 ovarioles each with a germarium at the tip, within which the germline and somatic stem cells are located. Two or three germline stem cells, located at the anterior tip of the germarium, divide asymmetrically to generate all germline cells in the ovariole (Wieschaus and Szabad, 1979; reviewed by Lin, 1997). Stem cell daughters known as cystoblasts undergo four rounds of synchronous division to produce groups of two, four, eight, and eventually 16 interconnected cystocytes, the precursors of ovarian follicles (reviewed by de Cuevas et al., 1997). Two somatic stem cells residing in the middle of the germarium give rise to all the somatic follicle cells (Margolis and Spradling, 1995); their equivalent in the testis are cyst progenitor cells. Three types of mitotically quiescent somatic cells are located in the vicinity of the stem cells: terminal filament and cap cells contact the germline stem cells, while inner sheath cells lie more posteriorly and contact both stem cell types.

Germline stem cell division is known to involve intrinsic mechanisms. This division and subsequent cystocyte divisions are physically unequal due to the segregation of fusomes rich in membrane skeleton proteins such as α-spectrin and an adducin homolog encoded by hu-li tai shao (hts) (reviewed by de Cuevas et al., 1997). The round fusome (or "spectrosome") characteristic of stem cells changes shape as cyst development proceeds, allowing cysts at different stages to be identified. The bag of marbles (bam) gene is highly expressed only in the stem cell daughter (McKearin and Spradling, 1990). The loss of Bam protein in cystoblasts prevents their differentiation, causing germline tumors to form (a "tumor" in Drosophila is a large clump of proliferating cells, the term does not imply these cells are cancerous). The genes pumilio (pum) and nanos (nos), encoding translational regulators, also play critical roles in the formation and maintenance of germline stem cells (Lin and Spradling, 1997; Forbes and Lehmann, 1998).

Less is known about the intercellular signals that control stem cell proliferation. Two important signaling molecules, Hedgehog (Hh) and Wingless (Wg) (reviewed by Perrimon, 1995; Cadigan and Nusse, 1997), are expressed in terminal filament and cap cells (Forbes et al., 1996a and 1996b). Hh signaling is critical for proliferation and differentiation of follicle cells, but it remained to be determined at the time the present invention was made whether somatic stem cells or their daughters are regulated (Forbes et al., 1996a and 1996b). The role of these signals in the germ line was even less clear because ectopic expression of hh did not appear to interfere with the function of germline stem cells (Forbes et al., 1996a).

Members of the transforming growth factor-β(TGF-β) family, including TGF-βs, activins, and the bone morphogenetic proteins (BMPs), elicit a broad range of cellular responses including the regulation of cell division, survival, and specification of cell fates (reviewed by Massague et al., 1996; Hogan, 1996a). TGF-βs were previously identified as repressing the proliferation of stem cells as assayed by either in vitro cultures or in vivo ectopic expression (Potter and Leoffler, 1990; Morrison et al., 1997). Inactivation of BMP-4 and its receptor BMPR in mice resulted in embryonic lethality for homozygous mutants (Winnier et al., 1995; Mishina et al., 1995), but no effect on stem cells was noted.

Similarly dpp, encoding a vertebrate BMP-2/4 homolog in Drosophila, functions as a local signal as well as a long-distance morphogen to pattern the early embryo and adult appendages by regulating cell proliferation and cell fate determination (Padgett et al., 1987; reviewed by Lawrence and Struhl, 1996). dpp is expressed in an anterior subset of follicle cells, and is required for establishing egg shape and polarity during late stages of oogenesis (Twombly et al., 1996). But an effect of dpp on maintaining and propagating stem cells, instead of causing their differentiation, has not been previously shown.

Major participants in the dpp signaling pathway have been identified: saxophone (sax) and thick veins (tkv) encode type I serine/threonine kinase transmembrane receptors, whereas punt encodes a type II serine/threonine kinase transmembrane receptor (Brummel et al., 1994; Nellen et al., 1994; Penton et al., 1994; Xie et al., 1994; Ruberte et al., 1995; Letsou et al., 1995). mothers against dpp (mad), Medea (Med), and Daughters against dpp (Dad) encode a family of conserved TGF-β transducers (Sekelsky et al., 1995; Tsuneizumi et al., 1997; Hudson et al., 1998; Wisotzkey et al., 1998; Das et al., 1998; Inoue et al., 1998), collectively known as Smads. Smads are proteins which transduce signals on behalf of TGF-β family members, or inhibit TGF-β signal transduction. A paradigm for TGF-β signal transduction has been developed from several experimental systems (Heldin et al., 1997). In Drosophila, Dpp binds both type I and II receptors to allow the constitutively active Punt kinase to phosphorylate and activate type I kinases, which phosphorylate Mad. The phosphorylated Mad brings Med into the nucleus as a transcriptional activator to stimulate dpp target gene expression.

Enhancing Dpp or other BMP-like signaling activities can be achieved by reducing the presence of Dad-like proteins, such as human Smad6 and Smad7. Vertebrate Smad6 and Smad 7 interact with type I receptors, and are known to inhibit both TGF-β and BMP signaling in cultured cells and frog embryos. Thus, disinhibition of TGF-β family members by inhibiting certain Smads promotes BMP-like signaling cascades. Additionally, Dpp or other BMP-like signaling activities may be increased by enhancing the function of Dpp or BMP receptors, such as Sax, Tkv, and Punt in Drosophila, and BMP receptors BMPR-II, ActR-II, Act-IIB, BMPR-IA, and ActR-I in humans. Other downstream positive regulators of Dpp or BMP signaling include Mad, Med, Dad, and Schnurri proteins in Drosophila, and Smad1, Smad4 and Smad5 in humans. See review by Padgett (1999).

Therefore, to address the prior art's failure to identify and characterize factors involved in germline stem cell maintenance and propagation, we now disclose that a member of the TGF-β family of growth factors and its signaling pathway unexpectedly provide this essential function.

SUMMARY OF THE INVENTION

It is an object of the invention to maintain and/or propagate stem cells by stimulating signaling through a bone morphogenetic protein (BMP) signaling pathway. In this manner a population of stem cells can be maintained in vivo or in vitro, and/or expanded.

Methods for maintaining germline and somatic stem cells of an organism are provided by stimulating a bone morphogenetic protein (BMP) signaling pathway.

The signal transduction pathway associated with a BMP specifically binding to a receptor may involve phosphorylation of serine/threonine residues (e.g., kinases, phosphatases) and a cascade of components of the pathway (i.e., signal transducers such as, for example, transcription factors) which communicate that signal. For example, a signal may be communicated from BMP binding at the cell surface to the nucleus where gene expression of downstream targets are either activated or inhibited. Thus, BMP signaling may be modulated at one or more steps in this pathway, or by affecting upstream regulators or downstream targets of this signaling pathway. Modulation (i.e., stimulation or repression) of BMP signaling may be accomplished directly on the stem cell or indirectly through other cells in a mixed cell population (e.g., feeder layer).

Properties of the stem cell may be maintained by stimulating BMP signaling. Furthermore, stem cells may be increased in abundance and/or increased in lifetime by such stimulation. Conversely, stem cells or tumor cells in a population may be reduced in total number or concentration, or even eliminated at the limit of detection, by repressing BMP signaling.

Stem cells may also be propagated and isolated according to the invention.

Our invention addresses the problem of restricted access to and limited numbers of stem cells. The ability to maintain and to propagate stem cells facilitates genetic manipulation and the characterization of these rare cells.

DESCRIPTION OF SPECIFIC EMBODIMENTS

The present invention provides a method for maintaining and controlling the division of germline stem cells in which dpp can provide an essential role. Further, it provides a model of ovarian tumor formation in which overexpression of dpp produces ovarian stem cell tumors. Clonal analysis demonstrates that downstream components (i.e., signal transducers) of the dpp signaling pathway are required cell-autonomously in the germline stem cells for their division and maintenance. This invention also provides a method for control of a cellular niche by BMP signaling, in which germline stem cells are regulated by, for example, a dpp signal that likely derives from surrounding somatic cells.

Stem cells are thought to be regulated by positive and negative diffusible factors, but the functions of most of these factors have never been demonstrated in vivo. The present invention provides a method in which Dpp directly signals to maintain Drosophila germline stem cells and stimulate their division. The experiments of the examples were made possible by a clonal cell marking method that allows the function of stem cells and their progeny to be examined directly over many cell generations. In addition to the dpp signal, known components in the dpp signal transduction pathway were shown to be required in these adult stem cells. This action appears to be specific to stem cells, since germ cells lacking dpp pathway components were still able to form 16-cell cysts. The examples demonstrate that a TGF-β-like molecule functions as a stem cell growth factor.

dpp signal transduction is required for maintaining stem cells, on which Dpp may act in several distinct ways. Signaling prevents germline stem cells from differentiating into cystoblasts and gametes. The examples show that overexpressed dpp prevents stem cell differentiation, while reduction of dpp function promotes stem cell differentiation. An attractive candidate target of the dpp signal transduction pathway is the Bam protein, which is normally synthesized at much higher levels in cystoblasts than in stem cells (McKearin and Ohlstein, 1995). The forced expression of Bam in germline stem cells causes them to differentiate in a manner very similar to that caused by reductions in dpp signaling (Ohlstein and McKearin, 1997). Thus, dpp signaling may negatively regulate Bam protein levels in germline stem cells. Two other genes, pum and nos, are required to form and maintain germline stem cells (Lin and Spradling, 1997; Forbes and Lehmann, 1998). In the embryo, both proteins work together to repress the translation of target genes such as hunchback (hb) (Baker et al., 1992; Murata and Wharton, 1995). In the ovary, dpp signaling may downregulate Bam through effects on the Nos/Pum pathway or by an independent mechanism. However, genes throughout the dpp pathway are required, including two nuclear transcription factors, suggesting that the action of the pathway is on transcription of target genes. Also see reviews by Attisano and Wrana (1998), Kawabata et al. (1998), and Padgett et al. (1998).

dpp may also function to maintain a specialized association between the stem cells and basal terminal filament cells. Such an association has been postulated to hold the stem cells at the anterior of the germarium, while daughter germline cells all move posteriorly and eventually leave the germarium. The results presented herein indicate that the stem cell loss is due to differentiation. Possibly, dpp signaling via its receptor regulates the expression of adhesion molecules that reside on the cell surface or of cytoplasmic proteins that indirectly promote stem cell adhesion.

dpp signaling also may act to stimulate stem cell division. dpp signaling stimulates cell proliferation at several points during Drosophila development. In the wing imaginal disc, it is essential for cell proliferation and/or survival (Burke and Baster, 1996), whereas it promotes the G2-M transition in the morphogenetic furrow of the developing eye disc (Penton et al., 1997). Consistent with such a requirement, mad mutants have greatly reduced imaginal discs, shortened gastric caeca, and small brains (Sekelsky et al., 1995). The requirement for dpp signaling disclosed herein suggests that adult stem cells use strategies similar to those of embryonic and larval somatic cells to regulate proliferation. For example, dpp stimulates the rate of cell division for stem cells.

During aging, the number and activity of stem cells are thought to be reduced. The examples indicate that the level of dpp signaling controls the life span and division rate of germline stem cells. Reduced dpp signaling caused premature stem cell loss. Perhaps more surprising is the observation that putative increases in signaling, caused by removal of Dad protein activity from stem cells, permitted stem cells to be maintained longer. This finding suggests that dpp signaling not only is necessary, but may sometimes be rate limiting for stem cell maintenance. The illustrative examples demonstrate for the first time a method in which stem cell life span has been extended in an intact organism.

These results suggest that it may be possible to extend the life span of stem cells, a process that could be of therapeutic significance. For example, drugs that upregulate BMP signaling to stem cells may enhance fertility in humans and animals, such as male fertility in patients with reduced numbers of germline stem cells (basal cells). Such drugs may ameliorate hematologic conditions caused by reduced stem cell functioning, for example aplastic anemias, agammaglobulinemia, and related conditions. Drugs enhancing BMP signaling may enhance wound healing. Aging-related pathologies caused by loss of stem cells, such as hair loss, loss of muscle mass, reduction of blood cell numbers, and the aging of the skin and other stem cell-dependent tissues could be treated by increasing BMP signal transduction. Compounds enhancing BMP signaling may increase the average lifespan of an organism.

One method for the enhancement of dpp signal transduction may be facilitated by removal of the dpp inhibitor Dad or other Dad-like inhibitory protein activity (inhibitory Smad activity) from the germline stem cells. Dad is induced by dpp signaling, but then acts to downregulate the very pathway that activated its production. This method could also be practiced with other negative regulators of the dpp signaling pathway and, in particular, inhibitory Smads. In contrast, brinker (brk) is a target gene repressed by dpp signaling and, because it is itself a transcriptional repressor, the net effect of repressing expression of the Brk repressor is to upregulate Brk-regulated target genes (Minami et al., 1999; Campbell et al., 1999; Jazwinska et al., 1999). This results in the increased production of Brk-regulated target genes following dpp signaling. Hence, BMP signaling can be stimulated or repressed by appropriate manipulation of Smads or target genes which are regulated by BMP signaling (i.e., increasing or decreasing their effects as appropriate to achieve stimulation or repression of BMP signaling). The roles of Dad and Brk, like the rest of the pathway, appear to be conserved in mammals.

Drugs that inhibit BMP signaling to stem cells may be useful chemotherapeutic agents. For example, drugs inhibiting BMP signaling pathways may be useful therapies against teratocarcinoma by causing stem cell differentiation. As another example, drugs which inhibit BMP signaling may be successful treatments against ovarian germline tumors dependent upon BMP signaling for continued growth.

Increased or decreased BMP signaling to stem cells might allow populations of stem cells to expand prior to bone marrow transplant, thereby increasing the chances of successful transplantation and reducing the amount of donor marrow required. Further, control of BMP signaling pathways may permit stem cells other than those in bone marrow to be removed from a patient, expanded in vitro, and subsequently reintroduced in to the patient to repair tissues damaged by injury or disease, such as Parkinson's disease.

Bone marrow from patients with hematologic tumors, such as lymphoma and leukemia, could be tested for BMP sensitivity. Positive test results for BMP sensitivity would allow steps to be taken to avoid potential side effects of anti-BMP treatment in vivo. For example, marrow removed from the patient could be cleansed of tumors cells by inhibiting BMP signaling, thereby inducing differentiation of tumor cells and reducing the tumor burden. The cleansed marrow would subsequently be returned to the patient in an autologous bone marrow transplant. Such differentiation therapy could also be used for solid tumors like sarcoma, carcinoma, and neuroglioma to reduce tumor burden. Therapy may be use alone or in association with other treatments such as, for example, chemotherapy, hyperthermia, or radiation which preferentially kills rapidly dividing cells and surgical resection of tumor.

Upregulation of BMP signaling to stem cells may permit the growth of germline stem cells in culture, useful in, for example, generating transgenic animals. Such techniques are especially useful in organisms which have not traditionally been used as genetic models of development and disease.

The ability to expand stem cell niches by overexpression of TGF-β members, such as dpp may allow rare human stem cells, or alternatively rare stem cells of any species, to be purified and propagated following transfer into living Drosophila, which have been genetically engineered to serve as hosts.

Beside biomedical research and treatment, other uses for the present invention include agriculture and wildlife conservation. Stem cells could be provided in or obtained from humans, primates (e.g., bonobo, chimpanzee, gorilla, macaque, orangutan), companion animals (e.g., dog, cat), and farm/laboratory animals (e.g., cattle, donkey, goat, horse, pig, sheep; amphibians such as frog, salamander, toad; birds such as chicken, duck, turkey, fishes such as carp, catfish, medaka, salmon, tilapia, tuna, zebrafish; lagomorphs such as hares, rabbits; rodents such as mice, rats).

Stem cells could be maintained and/or maintained in an appropriate niche or in culture, and used as a source of nuclei for cloning progeny organisms via nuclear transfer or a source of cells for propagation of mosaic organisms via embryo aggregation. Thus, Dpp or related BMPs provide a means for growing stem cells in vitro or in vivo for cloning animals.

BMP signaling is unlikely to be confined to one type of BMP and only type of BMP receptor because of the ability of evolutionarily diverged components of the BMP signal transduction pathway or different types of BMPs, BMP receptors, and SMADs to be functional equivalents of each other. For example, there appears to be crosstalk between Dpp/Tkv signaling and Gbb/Sax signaling (Haerry et al., 1998) and one signal transducer acts in different signaling pathways (Lagna et al., 1996). For example, a mixture of BMPs could be added to defined culture medium or be present in conditioned culture medium such that Dpp and Gbb would synergize in initiating BMP signaling through more than one different types of BMP receptor. As another example, one type of signal transducer could stimulate signaling through more than one different types of BMP receptor.

To stimulate BMP signaling, a positive signal transducer could be increased in expression (e.g., more transcripts and/or translated products) or mutated to a gain-of-function phenotype to increase activity of that signal transducer, while a negative signal transducer could be decreased in expression (e.g., fewer transcripts and/or translated products) or mutated to a loss-of-function phenotype to decrease activity of that signal transducer. Alternatively, a downstream target gene of BMP signaling could be directly activated or inhibited without BMP binding to its receptor by genetic engineering using a transactivator like GAL4 binding its UAS or ecdysone receptor binding upstream of the target gene. Similar techniques in mice involve induction with tetracycline or FK506.

Another method would be to increase endogenous BMP activity in the cells or to increase exogenous BMP activity outside the cells, especially if ligand is the limiting component in BMP signaling. For example, BMP expression may be increased in a stem cell and stimulate BMP signaling through an autocrine mechanism. Alternatively, BMP expression may be increased in a non-stem cell or a feeder cell, and then BMP activity could be secreted and taken up by the stem cell or brought into contact with the surface of the stem cell. BMP could also be added to the extracellular space or culture medium. BMP activity may be increased to stimulate BMP signaling by at least about 10%, 50%, 100%, or 200% as compared to the amount normally present in the animal or the culture.

Properties of the stem cell which may be maintained include the following: pluripotency, totipotency, committing to one or more differentiating cell lineages, giving rise to multiple different types of progenitors and/or differentiated cells, contributing to the germline and combinations thereof. Thus, the growth and/or survival of stem cells may be maintained without commitment to a program of differentiation, while retaining the capacity to differentiate normally under appropriate conditions following reduction or elimination of BMP signaling. More simply, stem cells in a population may be expanded in total number or concentration relative to non-stem cells (i.e., an increase in abundance), extended in the time between a stem cell's birth and its death or apoptosis (i.e., an increase in lifetime), or combinations thereof. Conversely, stem cells or tumor cells in a population may be reduced in total number or concentration, or even eliminated at the limit of detection, by repressing BMP signaling.

Stem cells made according to the present invention may be totipotent or pluripotent, male or female, germline or somatic, dividing or quiescent, vertebrate or invertebrate, present in situ or isolated, partially or substantially purified of differentiate cells, and combinations thereof. Proliferating stem cells are diploid, entering meiosis and the later stages of gametogenesis is part of the program of differentiation for male or female germline stem cells that is prevented by the present invention. Stem cells may be present in or obtained from testis, ovary, especially apical tips of Drosophila testes and/or ovarioles, or other adult or embryonic tissues. By differentiating, stem cells may differentiate into cells of the hematopoietic, immune, or nervous systems or the like. Preferably, stem cells maintained and/or propagated by the present invention retain the potential to later differentiate and thereby contribute to oogenesis or spermatogenesis, all three germ layers (i.e., endoderm, mesoderm, ectoderm), multiple differentiated cell lineages, and combinations thereof.

Somatic cells include terminal filament cells, cap cells, and inner sheath cells from the ovary and hub cells from the testis. Preferably, the present invention reduces the proportion of somatic cells in a population relative to germline cells during maintenance and/or propagation. A niche defined by surrounding somatic cells or a feeder layer comprised of somatic cells may provide cell contact and other extracellular signals to maintain and/or propagate germline cells. A feeder layer may be provided that provides certain essential extracellular signals by, for example, genetically manipulating cultured cells to express and secrete a BMP which then binds to its receptor on the stem cells.

Cell populations may be derived from the germline or somatic (or mixed) male or female, dividing or quiescent, vertebrate or invertebrate, present in situ or isolated, partially or substantially purified, and combinations thereof. Preferably, cell populations include cells expressing one or more BMPs; more preferably, BMP is secreted by non-stem cells and binds to receptors of stem cells to stimulate BMP signaling. Thus, stem cells of the present invention contain receptors for BMP, especially Dpp or a homolog, or are at least responsive to BMP signaling.

Besides mammals, amphibians, birds, and fishes, other organisms may be used in the present invention such as invertebrates like worms (e.g., Helminthes, Nematodes) and insects (e.g., Anopheles, Drosophila). In particular, comparison of components of the BMP signaling pathway, upstream regulators, and downstream targets show them to be highly conserved (Bitgood and McMahon, 1995; Padgett et al., 1998). Thus, the present invention should not be limited in its usefulness to Drosophila melanogaster. Other species which show conservation of dpp (Newfeld et al., 1997) and are likely to be useful are D. simulans, D. pseudoobscura, and D. virilis. For metazoan species in which there has been a diligent search, a dpp-like gene has been identified.

Mammalian homologs of dpp, glass bottom boat (gbb), and screw (scw) have been identified as BMP-2/4, BMP-5/8, and BMP-6, respectively (Hoffmann, 1997; Raftery and Sutherland, 1999; Wharton et al., 1999). A mammalian serine/threonine kinase receptor has been identified that specifically binds BMP-2 and BMP-4 (Yamaji et al., 1994). Other related members of the TGF-β family, their receptors, or other components of their signaling pathways, might also be used in the present invention. See also U.S. Pat. Nos. 5,011,691, 5,013,649, 5166,058, 5,168,050, 5,216,126, 5,324,819, 5,354,557, 5,635,372, 5,639,638, 5650,276, and 5,854,207.

Furthermore, mutational analysis and determination of structure-function relationships have identified conserved residues and essential residues for Dpp signaling (Wharton et al., 1996). Bacterially expressed Dpp can be refolded, then biochemically and biophysically characterized (Groppe et al., 1998). Homologs of a member of the BMP family, their receptors, and other components of the signaling pathway can be identified by a high level of structural conservation when amino acid sequences are compared, and/or functional conservation when homologs rescue mutant phenotypes or otherwise replace BMP activity.

Cell types have been identified by markers and are well characterized by genetic mutants and developmental studies. Stem cells may be provided in situ as part of an intact organism or they may be cultured in vitro. Germline stem cells and surrounding cells may be from an adult (e.g., ovary, testis) or an embryo. For in vitro culturing, cells may be obtained directly from an organism (i.e., primary culture) but it would be convenient to passage them through several cultures (e.g., at least five, ten, or twenty times) to expand their number (e.g., at least two, ten, or 100 times more than the original number).

Stem cells may be isolated from a donor organism with or without increasing cell number by stimulating BMP signaling; manipulated during transient in vitro culturing under conditions for maintenance and/or propagation by treating with one or more chemicals, introducing genetic material, fusing with another cell, mutating one or more genes, selecting a desired genotype or phenotype, or combinations thereof; and transplanting stem cells back into a host which is identical to the donor (i.e., autologous transplantation), similar to the donor but different (i.e., allogeneic transplantation), or is totally different from the donor (i.e., xenogeneic transplantation). In vitro culture conditions, genetic engineering of Drosophila by transfection and site-specific recombination, and cell or nuclear transplantation are known in the art.

For Drosphila, there are only about 10 germline stem cells per testis and about 32–48 germline stem cells per ovary (i.e., there are about 16 ovarioles per ovary and about two or three germline stem cells per ovary). The present invention provides greatly increased numbers of stem cells to be produced in vivo in an adult or embryo, and then cultured in vitro. In vitro culture of cells may be carried out by initially generating flies with a large number of germline stem cells in each ovariole. Then ovaries may be removed surgically into sterile culture medium and the germ cells released (they do not adhere and, thus, do not need to be disaggregated). Alternatively, disaggregated embryos may also be used as a source of germline stem cells. Although the number of germ cells per embryo is similar to the number per ovary and testis, it is possible to start with 100,000 embryos but only a few hundred gonads can be easily obtained. Schneider (1972) shows derivation of a cell line from Drosophila.

Drosophila cells may be plated into small wells containing feeder layers of cells expressing Dpp (e.g., Panganiban et al., 1990) or Hh (e.g., Lee et al., 1994), or culture media prepared by conditioning the media with cells secreting soluble factors or simply adding a recombinantly produced soluble factor (e.g., Dpp produced according to Groppe et al., 1998). In vitro culture media for growing Drosophila cells are commercially available such as, for example, Schneider's Drosophila medium. Drosophila cells can also be adapted and grown in mammalian tissue culture media (Spradling et al., 1975; Lengyel et al., 1975). Drosophila cells can be transfected like mammalian cells (Burke et al., 1984). Constructs and strategies for homologous recombination in somatic, embryonic stem (ES), and embryonic (EG) cells could be adapted for use with in vitro cultured Drosophila cells (Capecchi, 1989; Koller and Smithies, 1992). Cultured cells or their nuclei may then be transferred into Drosophila (Okada et al., 1974; Van Deusen, 1977).

Previous attempts at culturing germline stem cells utilized the 40 germline cells present in each embryo at a certain stage of development. But no dpp was provided, and these cells differentiated in culture (Allis et al., 1979). Inducing BMP expression in cells of such cultures or adding exogenous BMP to them would be a simple way of maintaining and/or propagating germline stem cells in vitro.

A BMP may also be used in replacement of, or combination with, known stem growth factors such as, for example, fibroblast growth factor (FGF), leukemia inhibitory factor (LIF), and steel factor (SF). Thus, BMP activity as observed herein might also be demonstrated using the techniques taught in U.S. Pat. Nos. 5,453,357 and 5,690,926.

Ex vivo culturing of stem cells with stimulation of BMP signaling only performed outside the body is preferred to avoid systemic effects of BMP signaling on the organism.

Vascular or organ engineering may be accomplished with stem cells that differentiate into endothelium or parenchyma, respectively, with or without an implantable support (e.g., stent, hollow fiber or particle) on which stem cells have been coated or impregnated. If not autologously transplanted and in an organism with an immune system recognizing histoincompatibility, transplantation of allogeneic or xenogeneic tissue may require immunosuppression of the host (e.g., cyclosporine A or FK506 treatment). Differentiation of stem cells into tissue with the activity and/or structure of adrenal gland, bone marrow, brain, liver, ovary or testis, pancreas, peripheral neurons or glia, red or white blood cells, skeletal or smooth muscle, skin, thyroid gland, or combinations thereof is preferred.

One or more genes of the stem cell may be activated or inhibited by chemical or environmental induction, antisense, ribozyme, chimeric repair vector, RNAi, or random/sequence-specific insertion. Ectopic expression of a gene may be controlled in a particular spatial or temporal manner, mimic pathologic or disease states, or create phenocopies of mutations in the endogenous gene. Homologous recombination is preferred to achieve gene knockout or replacement (see, e.g., U.S. Pat. Nos. 5,569,824, 5,602,307, 5,614,396, 5,683,906, and 5,830,682). For example, stem cells may be transfected with a polynucleotide, the polynucleotide or a portion thereof integrates into the genome of transfected stem cells at a random site or in a sequence-specific manner, homologous recombinants at a genetic loci of interest are selected, and the selected stem cells are transplanted into a host organism. Physical introduction of polynucleotides (e.g., biolistics, electroporation, microinjection) is preferred. Alternatively, insertion of P elements may be genetically engineered in vivo or in vitro in a stem cell maintained and/or propagated according to the present invention to disrupt genes (cf. Zhang and Spradling, 1994; Spradling et al., 1995).

TGF-β signaling has been shown to limit the growth of germline cysts during Drosophila spermatogenesis (Matunis et al., 1997). When punt or shn function is removed in clones of somatic cells that surround germ cells, cysts continue dividing after four rounds of mitosis (Matunis et al., 1997). However, these investigators did not address whether this pathway functions in male germline stem cells. In the embryo and imaginal discs, punt and shn can function downstream of dpp (Ruberte et al., 1995; Letsou et al., 1995; Arora et al., 1995; Grieder et al., 1995), but it was not known whether dpp or another TGF-β family member is utilized to send the signal. Clonal analysis of mutants in dpp downstream components in male germline stem cells, like those reported here in the ovary, could show whether Dpp and/or other TGF-β-like molecules are required for their division and maintenance in the testis.

In mouse, the BMP family members BMP-2 and -4 are most closely related to dpp, with greater than 75% identity, and can function to rescue dpp mutants in embryos (Padget et al., 1993). Recently, both genes have been inactivated by homologous recombination, but the homozygous embryos die too early to assess possible functions in the gonads (Winnier et al., 1995; Zhang and Bradley, 1996; reviewed by Hogan, 1996b). Consistent with our findings, Lawson et al. (1999) report that BMP-4 affects the number of primordial germ cells; moreover, BMP4 was needed in somatic tissue, and presumably stimulated BMP signal transduction in germline cells, although this was not shown directly. The roles during spermatogenesis of two other BMP family members, BMP-8A and BMP-8B, have been tested (Zhao et al., 1996; 1998). BMP-8B is required for the resumption of male germline cell proliferation in early puberty, and for germline cell survival in the adult, whereas BMP-8A plays a role in the maintenance of adult spermatogenesis.

The "niche" hypothesis postulates that stem cells reside in optimal microenvironments or "niches" (Schofield, 1978). When a stem cell divides, only one daughter can remain in the niche while the other becomes committed to differentiate. A stem cell within the niche would have a high probability of self-renewal, but a low probability of entry into the differentiation pathway. This model is consistent with the observations that stem cells require the addition of growth factors for proliferation and differentiation in many in vitro culture systems (Potter and Loeffler, 1990; Morrison et al., 1997). The molecular nature of the microenvironment within a niche has yet to be defined in any system, although the Drosophila germarium appears to contain such a niche. Anteriorly, the stem cells abut terminal filament and cap cells, which both express hh, while only the latter express armadillo (arm) and wg (Forbes et al., 1996a; 1996b). Stem cell daughters lie more to the posterior, and probably directly contact inner germarial sheath cells, which express patched (ptc) and hh (Forbes et al., 1996b). This asymmetry in structure and signals may allow germline stem cells to receive different levels of signals from their daughters. Consistent with the existence of a niche, two wildtype stem cells in germaria that recently lost a marked mutant stem cell were occasionally observed, suggesting that a vacated niche could be reoccupied.

The existence of the germline stem cell niche is also consistent with stem cell proliferation when local dpp is overexpressed. Under these conditions, the size of the niche may be substantially enlarged. Conversely, reduction of dpp function may weaken the ability of the niche to maintain germline stem cells, leading to accelerated losses. These results suggest that dpp is an essential niche signal. However, dpp likely interacts with other signals from surrounding somatic cells to make a functional niche for germline stem cells. Nonetheless, the identification of dpp as a key niche signal should greatly facilitate efforts to culture Drosophila germline stem cells in vitro.

Technical limitations have previously prevented identification of the source of the dpp signal that is received by germline stem cells. Ideally, analysis of clones of a null dpp allele would reveal which cells produce the signal. However, the somatic cells adjacent to the stem cells cease division early in ovary development and make induction of specific small clones difficult. The pattern of dpp expression in the germarium should also provide some insight into the origins of the signal. However, the only available dpp-lacZ fusion line and whole mount in situ experiments failed to detect expression in the germarium, although follicle cell expression in late stage egg chambers was observed. We now show that somatic cells in the niche express dpp. In many systems, low levels of dpp expression are known to be sufficient for biological effects so it may be sufficient to provide only low levels of BMP in the present invention.

In the Drosophila leg, antenna and genital discs, dpp and wg are induced in the anterior compartment by hh, and the mutual repression of dpp and wg restricts them to their appropriate domains (Brook and Cohen, 1996; Jiang and Struhl, 1996; Chen and Baker, 1996). In vertebrate limb development, sonic hedgehog (shh) can induce the expression of BMP-2 (Johnson and Tabin, 1995). The somatic terminal filament, cap, and inner sheath cells express hh and lie adjacent to the germline stem cells (Forbes et al., 1996a, 1996b). wg and dpp expression may be induced by hh, and signal to germline stem cells for their proliferation and maintenance. The data indicate that these and possibly additional signals from the anterior somatic cells define a niche for germline stem cells at the tip of germarium. Thus, agents which modify hedgehog signaling may be used to alter local BMP signaling, thereby regulating stem cell maintenance and/or propagation.

EXAMPLES

Example 1

Ectopic Dpp Expression Induces Germ Cell Tumors

To assess whether Dpp can regulate germline stem cells in the Drosophila adult ovary, Dpp was ectopically expressed in the germanium using hsp70-GAL4 (hs-GAL4) and UAS-dpp (Brand and Perrimon, 1993). To distinguish different cell types in the germarium, we used anti-Hts and anti-Vase antibodies to visualize somatic and germline cells, respectively. The anti-Hts antibody also recognizes spectrosomes and fusomes in the germline cells of the germarium (see de Cuevas et al., 1997).

Only germline stem cells and cystoblasts have a big round spectrosome, while cysts have a characteristic branched fusome. In the wildtype germarium, two germline stem cells are more anteriorly located than cystoblasts. Developing cysts in germarial regions 1 and 2a (i.e., the anterior half), which are more posterior than germline stem cells and cystoblasts, are connected by fusomes. In the germarial regions 2b and 3, both lens-shaped and round cysts span across the germarium, and become surrounded by somatic follicle cells. Fusome structures begin degeneration in these older cysts.

The germaria from hs-GAL4 females subjected to heat shock, and those from females carrying hs-GAL4 and UAS-dpp in the absence -of a heat shock, were indistinguishable from wildtype. In these heat shock-treated germaria, large single germline cells filling the corresponding wildtype germarial regions 1 and 2a contained spectrosomes but showed no evidence of cyst formation. In the corresponding wildtype regions 2b and 3, both lens-shaped and round cysts were observed that probably derived from differentiated cystoblasts or cysts that had formed before the initial heat shock.

Consistent with this interpretation, after 4–5 days of heat shock, all germline cells in the corresponding regions 1 and 2 were single cells containing spectrosomes and developing cysts containing branched fusomes were rarely detected. Only somatic follicle cells were detected, there were no germline cells. This phenotype is very similar to that of bam and benign gonial cell neoplasm (bgcn) mutants (McKearin and Spradling, 1990; Gateff and Mechler, 1989).

Here, instead of the wildtype number of two or three germline stem cells per ovariole, dozens were present in a single ovariole. Moreover, the number present was 2–3 times greater after 4–5 days than after 3 days. Because there are 16 ovarioles per ovary and two ovaries per female fly, all of the above numbers should be multiplied by 32 to calculate the number of female germline stem cells per fly. The germline stem cells proliferate following induction of dpp to form a large mass of normal appearing, normal functioning germline stem cells. The proliferating cells were shown to be germline stem cells based on (1) general size and appearance, (2) fusome morphology, (3) expression of the germ cell-specific gene vasa, (4) absence of expression of cytoplasmic Bam (i.e., a sensitive indicator that germline stem cells have differentiated into cystoblasts), and (5)

ability to differentiate along the normal pathway for germline cells following removal of dpp.

Example 2
Dpp-induced Tumor Cells Resemble Germline Stem Cells

Cystoblasts and early mitotic cysts can be distinguished from stem cells because the former express cytoplasmic Bam protein from the cystoblast stage to the end of the 8-cell stage cyst stage. Immunofluorescent staining of the wildtype germarium with anti-BamC and anti-α-spectrin antibodies document that cystoblasts and developing cysts, but not germline stem cells, express cytoplasmic Bam protein. Immunofluorescent staining of dpp-induced germaria with anti-BamC and anti-α-spectrin revealed that amplified single germline cells failed to express the cytoplasmic Bam protein. In dpp-induced germaria, a few, rare BamC-positive cells were observed that appeared to be growing cysts. These data show that the large number of single germline cells induced by dpp overexpression resemble stem cells rather than differentiated cystoblasts.

To determine that this absence of BamC-staining was not due to growth arrest of the accumulated single germline cells, dpp-induced germaria were stained with anti-BrdU and anti-α-spectrin antibodies following incorporation of the nucleotide analog BrdU for one hour. Mitotically active germline cells in their S-phase of the cell cycle can incorporate BrdU. In the dpp-induced germaria, some single germline cells incorporated BrdU, indicating that these single germline cells have not undergone growth arrest.

These results show that the tumor cells induced by dpp overexpression continue to divide, and resemble stem cells in their fusome morphology and absence of Bam protein. They represent an increased number of germline stem cells.

To determine if these dpp-induced stem cells retain the capacity to differentiate, their behavior was examined. hs-GAL4/UAS-dpp Drosophila were induced by four days of heat shock-treatment, and then returned to room temperature for 2 or 4 days prior to staining with anti-Hts and anti-Vase antibodies. Germline cysts were observed starting to form two days after the temperature downhift and always formed initially in the most posterior region of the tumor. Many 16-cell cysts were seen 4 days after the shift back to room temperature. Based on their location and number, these cysts must derive from dpp-induced germline stem cells, rather than from stem cell divisions that occur after the down-shift. But not all the dpp-induced germline stem cells were able to form complete cysts, because some ovarioles contained cysts with one, two, four, or eight cells in region 3.

Example 3
Overexpressed dpp Acts Directly on Germline Stem Cells

Two different models could explain the Dpp effect on germline stem cells: direct signaling to the germline stem cells and relay signaling. The relay signaling model predicts that ectopic Dpp turns on a secondary signal in the somatic cells surrounding germline stem cells.

To directly test the relay model, the hs-GAL4/UAS system was used to activate Dpp type I receptors. The hs-GAL4/UAS system can express a target gene at high levels in somatic cells of the adult ovary, but not in germline cells (Manseau et al., 1997). Both activated tkv (tkv*) (Nellen et al., 1996) and activated sax (sax*) (Des et al., 1998) have been shown to mimic dpp signaling pathway activation in many developmental processes.

Overexpression of activated Dpp type I receptors in the somatic cells of the germarium does not mimic the effect of ectopic dpp expression. Flies of the following genotypes were subjected to heat shock-treatment for three days, and germaria were subsequently labeled with anti-Vase and anti-Hts antibodies: hsGAL4/UAS-sax*, hsGAL4/UAS-tkv*, and UAS-sax*/+;hsGA4/UAS-tkv*. Two independent lines containing the UAS-tkv* and UAS-sax* insertions at different chromosomal sites were tested. When activated sax* or tkv*, or both, were overexpressed in the somatic cells of the germarium using hs-GAL4, the same driver for dpp overexpression, no germline stem cell proliferation was observed. But egg chamber budding was frequently affected in region 3 cysts in the hsGAL4 UAS-tkv*, and UAS-sax*/+;hsGAL4/UAS-tkv* lines, suggesting that somatic follicle cell function was defective at a later stage.

These results suggest that relay signaling, regardless of its mechanism, is by itself not sufficient to inhibit germline stem cell differentiation. Since overexpressed Dpp does not appear to act by a relay signal, it likely acts directly on germline cells via functional Dpp receptors to inhibit cystoblast differentiation.

Example 4
Dpp and Sax are Required for Germline Stem Cell Division and Maintenance To directly test the role of dpp, we examined mutations that reduce its function and that of the Dpp receptor sax. Dpp signaling is essential at many points during Drosophila development. Several temperature-sensitive allelic combinations of dpp mutants, including $dpp^{e90}/dpp^{hr56}$ and $dpp^{hr\,4}/dpp^{hr\,56}$, can develop into adults at 18° C. (Wharton et al., 1996). These heteroallelic combinations allowed us to examine the mutant phenotypes of dpp in the germarium after the shift to 28° C. Forty to 50% of germaria from these genotypes examined one week after the temperature shift were significantly smaller than heterozygotes, and more severe reductions were seen in older females maintained at the higher temperature. To determine if stem cells were being lost, ovaries from the mutant females were stained with anti-Hts and anti-Vase antibodies and the number of stem cells in each ovariole were directly counted (Table 1). There was a dramatic reduction in germline stem cell number in both tested genotypes over a two week period. The stronger of the two, $dpp^{hr\,4}/dpp^{hr\,56}$, almost completely eliminated stem cells within two weeks. This combination produces many fewer adult flies and is known to disrupt embryonic development more severely than $dpp^{e90}/dpp^{hr56}$ (Wharton et al., 1996).

If the mutations act specifically on germline stem cells, cystoblasts and cysts should continue to divide and develop. To examine this, the morphology of fusomes in the mutant ovarioles were analyzed. Ovarioles from the Dpp receptor mutant $sax^P$, which has a weaker effect on stem cell number were also studied. The timing of stem cell loss is expected to vary among individual germaria, because stem cell loss is a random process (Margolis and Spradling, 1995).

Control germaria from one week-old $sax^P/+$ and $dpp^{e90}/CyOP23$ females were double labeled with anti-Vase and anti-Hts antibodies. In both cases, germaria from one week-old females heterozygous for the dpp or sax alleles generally contained two stem cells at the anterior. The mutant germania were also double labeled with anti-Vase and anti-Hts antibodies.

Mutant $sax^P/sax^P$ germaria from one week-old females were smaller than wildtype. In one case, two stem cells were observed but the number of cysts was reduced. In another case, one stem cell remained and regions 1 and 2a were much reduced as indicated by the start of region 2b. This indicates that stem cells were being lost and their division slowed.

Many germaria in two week-old mutant $sax^P/sax^P$ females had lost both stem cells and no mitotic cysts were present, although cysts and egg chambers at later developmental stages remained (e.g., the most anterior cyst corresponding to region 2b).

Mutant $dpp^{e90}/dpp^{hr56}$ females showed a more rapid loss of stem cells at 28° C. Such germaria frequently contained one or zero stem cells after one week. In one case, only one stem cell and no mitotic cysts were found; the most anterior cyst contained 16 cells. In another case, no stem cells were present; an 8-cell cyst and a 16-cell cyst lay at the anterior. After two weeks, most ovarioles lacked stem cells entirely, but some still contained 16-cell cysts or older follicles.

Because normal cystocyte development continued throughout the germarium, the effects of these mutations appear to be limited largely to stem cell division and maintenance. Some abnormalities in a later process, egg chamber budding, were observed. Stem cell loss might be caused by either cell death or differentiation. Apoptotic cells were not observed in the most anterior region of these germaria where germline stem cells are located based on DAPI staining.

These results indicate that a reduction in the level of dpp signaling promotes the differentiation of germline stem cells into cysts, and thus causes stem cell loss. Consistent with previous studies (Twombly et al., 1996), we observed some partially ventralized eggs with anterior defects in these dpp mutants and the $sax^P$ mutant.

Example 5
Put, Tkv, Mad, Med, and Dad are Required Cell-Autonomously for Germline Stem Cell Maintenance To demonstrate definitively that dpp signaling was received by the germ line, studies were conducted to assess whether components of the signal transduction pathway are autonomously required in these cells. Flp-induced mitotic recombination was employed to generate marked clones homozygous for loss-of-function mutations in the germline stem cells of adult ovaries (see Experimental Procedures). Genes downstream of dpp in the signal transduction pathway are required in the germline stem cells for their division and maintenance. Germaria lacking or bearing stem cell clones of the indicated genotypes were generated, and then labeled with anti-lacZ and anti-Hts antibodies. Marked stem cells and their progeny cysts were indicated by the absence of lacZ protein.

Clones were marked using armadillo-lacZ, which is strongly expressed in all cells within the germarium when wildtype flies are not subjected to heat shock. Stem cell clones can be recognized because only stem cells persist in the germarium more than 5 days after a mitotic recombination event (Margolis and Spradling, 1995). As recombination events can take place only in mitotically active adult cells, this method will not produce mutant clones in the terminally-differentiated terminal filament, cap cells, and inner sheath cells. Consequently, this approach excludes potential complications due to mutant clones in these surrounding somatic cells, allowing the autonomous function of genes to be tested in germline stem cells. This method has three major additional advantages. Firstly, the persistent mutant clones can be studied over a long period of time allowing germline stem cell maintenance to be quantified. Secondly, the existence of both a mutant and a wildtype stem cell side-by-side in the same germarium provides a control for the effects of gene removal by direct comparison. Thus, the relative division rates of these two stem cells can be determined simply by counting the number of mutant and wildtype cysts in germania with one mutant and one wildtype stem cell. Finally, germline stem cell-specific effects of the mutations can be assessed by looking at the developmental status of marked cystoblasts, cysts, and egg chambers.

Germline stem cell clones of punt-, tkv-, mad-, Med-, and Dad- were generated by subjecting females of the appropriate genotype to heat shock and examining their ovaries beginning one week later. Stem cells in the Drosophila ovary have a finite life span with a half-life of about 4.6 weeks (Margolis and Spradling, 1995; Table 2). In contrast to wildtype clones, stem cells mutant for each of the tested genes (except Dad) were lost more rapidly (Table 2). For example, after one week, the $punt^{135}$ mutant germline stem cell was either still present or had only recently been lost, as indicated by the presence of relatively young mutant cysts. However, after two weeks, the $punt^{135}$ mutant germline stem cell had usually been lost and only a few advanced mutant cysts remained.

$mad^{12}$ mutant stem cells were lost even more rapidly. After one week, the $mad^{12}$ mutant germline stem cell sometimes remained, but did not proliferate well as indicated by the lack of progeny cysts. More frequently, the germline stem cell was already lost and a more developed cyst (or cysts) was observed. After two weeks, $mad^{12}$ mutant germline stem cells rarely remained so there were no mutant cysts, but older mutant egg chambers were present. Surprisingly, two wildtype germline stem cells were occasionally observed after the mutant stem cell was lost. These results indicate that the dpp signal directly acts on germline stem cells to regulate their maintenance. However, no effects were observed on the formation of 16-cell cysts or the subsequent development of germline cells.

Unlike the other tested genes, Dad is a negative regulator of dpp signaling. The Dad gene is induced by the dpp signaling pathway and antagonizes the function of dpp (Tsuneizumi et al., 1997). The $Dad^{271-68}$ allele is a severe allele in which the entire C-terminal conserved domain was deleted (Tsuneizumi et al., 1997). Strikingly, germline stem cells mutant for $Dad^{271-68}$ were not lost (e.g., a mutant germline stem cell and its progeny cysts may be present), even if both germline stem cells lacked this gene (e.g., two mutant germline stem cells and a normal complement of progeny cysts were present). No turnover could be detected even after three weeks of clone induction, suggesting that increasing dpp signaling can prolong germline stem cell lifetime.

To compare the magnitude of the effects of different mutations on stem cells, the half-life of mutant germline stem cells was measured (Table 2; Experimental Procedures). $punt^{10460}$ is a hypomorphic allele of the Dpp type II receptor whereas $punt^{135}$ is a strong allele (Arora et al., 1995; Letsou et al., 1995). In $punt^{10460}$ clones, germline stem cell half-life was reduced from about 4.6 to 0.90 weeks, whereas the stronger $punt^{135}$ allele reduced germline stem cell half-life to about 0.41 weeks. $tkv^8$ is a strong allele of the type I receptor (Brummel et al., 1994; Nellen et al., 1994; Penton et al., 1994). $tkv^8$ stem cell clones reduced germline stem cell half-life to about 0.69 weeks. Clones of two alleles of the downstream signal transducer, $mad^9$ and $mad^{12}$, reduced germline stem cell half-life to 2.5 weeks and 0.25 weeks, respectively. Consistent with this observation, $mad^{12}$ is a much stronger allele than $mad^9$ (Sekelsky et al., 1995). $Med^{26}$ is a strong allele of another downstream transducer (Des et al., 1998). $Med^{26}$ germline stem cells turned over with a half-life of about 0.38 weeks.

Example 6
Punt, Tkv, Mad, Med are Required Cell-Autonomously to Stimulate Germline Stem Cell Division To further define the role of the dpp pathway in the regulation of germline stem cell division, the number of mutant and wildtype cysts in germaria carrying one mutant and one wildtype germline stem cell were compared. Since each cyst represents one germline stem cell division, counting the number of wildtype and mutant cysts allowed the measure of relative germline stem cell division rates. All germaria that still retained a mutant germline stem cell from all three time points were counted and compared to the number of wildtype cysts. In controls containing a marked but genetically wildtype germline stem cell, approximately 50% of cysts were marked, indicating that two germline stem cells are present in one week-old adult germaria and divide at similar rates (see Table 2).

As expected based on previous experiments punt-, tkv-, mad-, and Med- mutant germline stem cells all divided more slowly than wildtype (see Table 2). While the relative division rate of marked wildtype germline stem cells was about 0.93, the rates in the tested genotypes ranged from about 0.21 to 0.60. These reductions mostly correlated with the known strength of these alleles, and with their effects on germline stem cell maintenance. However, both $punt^{10460}$ and $punt^{135}$ mutant germline stem cells proliferated about three-fold slower than the wildtype, despite the fact that they differ in strength. Differences between the effects of these mutants on maintenance and division may reflect branch points in the pathway, and may suggest that at least one additional type II receptor also mediates germline stem cell behavior. Interestingly, $Dad^{271-68}$ mutant germline stem cells, which were more stable than wildtype, divided at a similar or slightly slower rate than wildtype ones. These results demonstrate that components of the dpp signaling pathway are required autonomously for the proliferation of germline stem cells.

As shown previously, cysts produced in the presence of overexpressed dpp driven by hs-GAL4 always contained 16 cells. To verify that dpp signaling is not involved in regulating the cystoblast and cystocyte divisions, the number of germline cells in individual cysts mutant for $pun^{10460}$, $mad^9$, $mad^{12}$, $Med^{26}$, and $Dad^{271-68}$ were counted. in every case, these cysts contained 16 cells, including a single oocyte. Therefore, the dpp signaling pathway specifically acts on stem cells within the germ line.

Example 7
Dpp is Expressed in Differentiated Somatic Cells Surrounding Germline Stem Cells.

To directly localize the source of the Dpp signal, a whole mount mRNA in situ hybridization was performed to visualize expression of the dpp gene on two day-old wildtype females which were dissected and fixed. A standard protocol was used (Yue and Spradling, 1992) except that protease digestion was performed at 50 gm/ml for 5 min. No staining was observed using the dpp sense RNA probe as a control. Under the same conditions, the dpp anti-sense probe detected the dpp mRNA in the inner sheath cells and cap cells adjacent to germline stem cells, and in the posterior somatic follicle cells, but not in germline and terminal filament cells. These expression data further support our finding that surrounding differentiated somatic cells constitute a niche for germline stem cells.

Example 8
A Lost Germline Stem Cell can be Replaced by the Daughter of the Other Stem Cell in the Same Germarium To provide further evidence that the stem cells in the ovariole reside within a niche, we showed that lost germline stem cells can be replaced and function as germline stem cells by cells that would otherwise differentiate. In one week-old germaria in which one stem cell is marked, the marked cell contributes almost 50% of cysts, suggesting there are an average of two germline stem cells per germarium. Since we have shown that wildtype germline stem cells turn over with a half-life of 4.6 weeks, ovarioles containing only one or zero germline stem cells would arise at a predictable rate unless they are replaced. For example, after 4.6 weeks, 25%, 50% and 25% of the germaria are expected to have two, one, and zero germline stem cells. In contrast, we observed that more than 71% of five week-old germaria still contain two germline stem cells, 20% contained one germline stem cell, and 9% contained none. These results were unexpected and demonstrate that following loss, germline stem cells are replaced 62% of the time over this time period.

To determine how replacement occurs, we identified ovarioles where a marked stem cell had just been lost and was in the process of being replaced Such ovarioles contain a marked cystoblast and marked developing cysts, but no marked stem cell. We observed an unusual division of the remaining stem cell in a plane perpendicular to the axis of the ovariole. Such a division would place the stem cell daughter in the same location as the recently lost stem cell. Normally, a germline stem cell divides along the anterior-posterior axis, and the posterior daughter differentiates into a cystoblast. These findings indicate that the fate of the stem cell daughter is determined by the environment. This environment within the niche maintains the stem cell fate, while the environment more posteriorly in the ovariole promotes differentiation as a cystoblast.

Example 9
Dpp is Required for Maintenance of Male Germline Stem Cells

Temperature sensitive dpp mutant genotypes were generated by crossing $dpp^{hr56}$/CyO with $dpp^{hr4}$ and $dpp^{e90}$/CyO. Temperature-sensitive punt mutant males were generated by crossing $punt^{10460}$/TM3 with $punt^{135}$/TM3 Sb. The $dpp^{hr56}$/$dpp^{e90}$, $dpp^{hr\ 56}$/$dpp^{hr\ 4}$ and $punt^{10460}$/$punt^{135}$ adult males were raised at 28° C. (i.e., the restrictive temperature) for one week. Heterozygotes controls were also examined at 28° C.; testes were dissected out and stained with rabbit anti-Vasa and mouse anti-Hts antibodies. Cy3-conjugated goat anti-rabbit and FITC-conjugated goat anti-mouse secondary antibodies were used to visualize the Vasa protein (red) and Hts protein (green) with a Leica TCS-NT confocal microscope. The germline stem cells are located at the tip of testes, and can be recognized by their expression of Vasa protein (red) and also contain round fusomes (yellow), and by their association with hub cells (green). The differentiated germline cells lie more distant from the tip, and also contain either round fusomes or branched fusomes.

To directly show that dpp regulates male germline stem cells in Drosophila testes, the number of stem cells was examined in $dpp^{hr56}$/$dpp^{e90}$,$dpp^{56}$/$dpp^{hr4}$ and $punt^{10460}$/$punt^{135}$ mutant testes under restrictive conditions, and compared to heterozygote control testes. In a heterozygous testis (control), there were between seven and nine germline stem cells located adjacent to somatic hub cells and contain round fusomes like their counterparts in the ovary; these testes were full of developing germline cysts and primary spermatids. After one week at the restrictive temperature, there were still over seven germline stem cells. These values are indistinguishable from the typical wildtype testis. In contrast, one week-old dpp$^{hr\ 56}$/dpp$^{e90}$,dpp$^{hr\ 56}$/dpp$^{hr\ 4}$ and punt$^{10460}$/punt$^{135}$ mutant testes from males that had been raised at the restrictive temperature contained a reduced number of germline stem cells, ranging in number from 2–7 per testis. As a consequence of this loss, these testes were also significantly smaller than the controls and contained fewer developing germline cysts and primary spermatids. Because a testis starts with a much larger number of germline stem cells than an ovariole, complete loss would not be expected within one week even if they require dpp and punt to the same degree as female germline stem cells. These results demonstrate that dpp and punt are required for maintaining male germline stem cells.

Example 10
Shn is Required for Germline Stem Cell Maintenance schnurri (shn) encodes a zinc-finger protein homologous to human MPB1. It is required for dpp signaling in the Drosophila embryo (Arora et al., 1995; Greider et al., 1995). Mutant shn germline stem cell clones were generated as described above. FRT42D arm-lacZ/FRT42D arm-lacZ virgin females were crossed to FRT42D shn/CyO and FRT42D+/FRT42D+(control) males, respectively. Two day-old adult non-CyO females carrying an arm-lacZ transgene in trans to the shn mutant-bearing chromosomes were heat shocked twice at 37° C. for 60 min each separated by eight hours. Germline stem cells were examined in the same manner as described above. These results demonstrate that shn is also required in germline stem cells for their maintenance and division.

Experimental Procedures

A description of materials and methods useful for practicing the present invention is given in the following general references: Lindsley and Grell (*Genetic Variations of Drosophila melanogaster*, Carnegie Inst. of Wash., 1968); Ashburner (*Drosophila: A laboratory handbook and A laboratory manual*, Cold Spring Harbor Lab., 1989); Lindsley and Zimm (*The Genome of Drosophila melanogaser*, Academic, 1992); Bate and Arias (*The Development of Drosophila melanogaster*, Cold Spring Harbor Lab., 1993); and Greenspan (Fly Pushing: *The Theory and Practice of Drosophila Genetics*, Cold Spring Harbor Lab., 1997). Drosophila stocks may be obtained from the Bloomington Stock Center at Indiana University. Information relevant to Drosophila genetics and molecular biology, including recombinant clones and nucleotide/amino acid sequences obtained through the Drosophila genome project, is publicly available in the FLYBASE relational database (see Nucl. Acids Res. 27, 85–88, 1999).

Drosophila Stocks and Genetics

The following fly stocks used in this study were described either in the FlyBase or otherwise specified: tkv$^8$; punt$^{10460}$ and punt$^{135}$; mad$^9$ and mad$^{12}$; Med$^{26}$ (Des et al., 1998); Dad$^{271-68}$, sax$^P$; dpp$^{hr56}$ dpp$^{hr4}$, dpp$^{e90}$; UAS-dpp; hs-GAL4; HSFlp; FRT40A armadillo-lacZ and HSFLP;FRT82B armadillo-lacZ (Lecuit and Cohen, 1997); UAS-tkv* (activated) and UAS-sax* (activated) on both chromosomes 2 and 3 (Des et al., 1998). Most stocks were cultured at room temperature. To maximize their effects, sax$^P$ and dpp mutants were cultured at 28° C. for 1–2 weeks.

Generating Mutant Germline Stem Cell Clones and Overexpression

Clones of mutant cells were generated by Flp-mediated mitotic recombination as described previously (Xu and Rubin, 1993). To generate the stocks for stem cell clonal analysis, +FRT40A/CyO, tkv$^8$FRT40A/CyO, mad$^9$ FRT40A/CyO, and mad$^{12}$ FRT40A/CyO males were mated with virgin females w HSFlp1; armadillo-lacZ FRT40A, respectively FRT82B Med$^{26}$/TM3 Sb, FRT82B punt$^{135}$/TM3 Sb, FRT82B punt$^{10460}$/TM3 Sb, FRT82B Dad$^{271-68}$/TM3 Sb males were mated with virgin females w HSFlp1; FRT82B armadillo-lacZ, respectively. Two day-old adult non-CyO or non-Sb females carrying an armadillo-lacZ transgene in trans to the mutant-bearing chromosome were heat shocked at 37° C. for 60 min. The females were transferred to fresh food every day at room temperature, and ovaries were removed one week, two weeks, or three weeks after the last heat shock-treatment and processed for antibody staining.

To construct the stocks for overexpressing dpp and activated receptors, the hs-GAL4 virgins were crossed with UAS-dpp, UAS-tkv*/CyO, UAS-tkv*/TM3 Sb, UAS-sax*/CyO, UAS-sax*/TM3 Sb, UAS-tkv*/CyO; UAS-sax*/TM6, UAS-sax*/CyO; UAS-tkv*/TM6 males, respectively. The females which did not carry balancer chromosomes were heat shocked at 37° C. for 30 min each time with the interval of 12 hr for 3–5 days.

Calculations

To determine stem cell life spans, stem cells were marked in one to two day-old females of the appropriate genotype by a single heat pulse. Subsequently, ovaries were dissected from some of the females one, two, and three weeks later and stained with anti-Hts and anti-lacZ antibodies. The percentage of germaria containing a marked stem cell was determined by counts of 60–200 germaria at each time point, and used to calculate the stem cell half-life.

To measure stem cell division rates, we determined the relative number of wildtype and mutant cysts in germaria that contained one wildtype and one mutant stem cell. A relative division rate of 1.0 would indicate normal division. For a given genotype, these values were similar at each time point, and the average is presented in Table 2. Marked wildtype stem cells gave a value of 0.93 rather than 1.0 probably due to a small fraction of germaria that contained three rather than two germline stem cells.

To measure stem cell loss, germaria with two, one, or no germline stem cells, were counted from the ovaries of the one and two week-old females. Heterozygous females carrying one copy of the mutant gene in combination with a CyO balancer chromosome containing a dpp transgene (Hursh et al., 1993) served as a control. Values are expressed as the percentage of ovarioles with the indicated stem cell compositions.

Immunohistochemistry

The following antisera at the indicated dilutions were used: polyclonal anti-Vasa antibody (1:2000) (Liang et al., 1990); monoclonal anti-Hts antibody 1B1 (1:5) (Zacci and Lipshitz, 1996); polyclonal anti-α-spectrin antibody (1:100) (Byers et al., 1987); rat anti-Bam antibody (1:100) (McKearin and Ohlstein, 1995); monoclonal anti-BrdU antibody (1:50) (Becton-Dickinson); polyclonal anti-β-galactosidase antibody (1:1000) (Cappel). Labeling with BrdU was carried out for 1 hour at room temperature as described by de Cuevas and Spradling (1998). All photomicrographs were taken using a Leica TCS-NT confocal microscope.

TABLE 1

Dpp is Required for Germline Stem Cell Maintenance.

| | One week | | | Two weeks | | |
|---|---|---|---|---|---|---|
| Genotypes | No GSC | One GSC | Two GSC | No GSC | One GSC | Two GSC |
| $dpp^{e90}$/CyOP23 | 0.0% (0) | 4.4% (5) | 95.6% (108) | 0.5% (1) | 17.5% (36) | 82.0% (168) |
| $dpp^{hr4}$/CyOP23 | 0.0% (0) | 3.5% (6) | 96.5% (165) | 1.5% (3) | 23.9% (48) | 74.6% (150) |
| $dpp^{e90}$/$dpp^{hr56}$ | 16.0% (17) | 29.3% (31) | 54.7% (58) | 47.3% (140) | 39.8% (118) | 12.9% (38) |
| $dpp^{hr4}$/$dPP^{hr56}$ | 18.1% (22) | 33.9% (41) | 48.0% (58) | 98.4% (122) | 1.6% (2) | 0.0% (0) |

The percentage of ovarioles with zero, one or two germline stem cells is given for each genotype. Actual numbers are given in parentheses.
<sup>a</sup>P23 is a dpp transgene on the CyO chromosome (Hursh et al., 1993).

TABLE 2

Downstream Components of the dpp Pathway are Required in Germline Stem Cells for their Maintenance and Division.

| | Percent of Germaria[a] with a Marked GSC | | | GSC[b] Half-Life | Relative[c] Division |
|---|---|---|---|---|---|
| Strains | 1 week | 2 weeks | 3 weeks | (weeks) | Rate |
| Control | 37.7 (138) | 34.4 (161) | 27.5 (160) | 4.6 | 0.93 (1410) |
| $punt^{10460}$ | 43.2 (118) | 26.4 (182) | 9.5 (116) | 0.90 | 0.36 (1126) |
| $punt^{135}$ | 27.4 (95) | 5.1 (138) | 0 (114) | 0.41 | 0.37 (329) |
| $tkv^8$ | 38.6 (132) | 16.4 (176) | 6.1 (197) | 0.69 | 0.29 (744) |
| $mad^9$ | 43.6 (g4) | 29.3 (208) | 25.8 (155) | 2.5 | 0.60 (1116) |
| $mad^{12}$ | 17.8 (124) | 0 (108) | 0.7 (136) | 0.25 | 0.21 (214) |
| $Med^{26}$ | 23.8 (172) | 7.3 (110) | 0 (122) | 0.38 | 0.39 (512) |
| $Dad^{271-68}$ | 28.0 (107) | 32.6 (86) | 32.3 (62) | >>4.6 | 0.84 (770) |
| Control | 41.3 (235) | 33.8 (185) | 32.1 (379) | 4.7 | 1.16 (316) |
| shnP | 38.9 (126) | 23.7 (228) | 16.5 (332) | 2.2 | 0.53 (331) |

[a]Number of germaria with lacZ-negative germline stem cell clone / total germaria × 100. The actual number of germaria counted is given in parentheses.
[b]Calculated as described in Experimental Procedures.
[c]Calculated as described in Experimental Procedures. The number of cysts counted is given in parentheses.

While the present invention has been described by what is presently considered to be practical and preferred embodiments, it is to be understood that variations in the claimed invention will be obvious to skilled artisans without departing from the novel aspects of the present invention and that such variations are intended to come within the scope of the claims.

For example, components of the dpp signaling pathway are conserved in structure (e.g., amino acid residues are identical or chemically analogous in a high proportion of positions when sequences are aligned) and function such that mammalian proteins can rescue Drosophila mutant phenotypes which result from mutations in homologous gene of the pathway. Equivalents to the Drosophila genes and proteins identified herein, as well as mutants thereof, would be known to skilled artisans practicing the present invention by their similarity in amino acid sequence (e.g., members of the TGF-β family) and/or their ability to at least partially rescue mutant phenotypes or to create phenocopies of such phenotypes.

Thus, the extent of legal protection will be determined by the limitations recited in the allowed claims and their equivalents. Unless explicitly recited, other aspects of the present invention as described in this specification do not limit the scope of the claims. In this regard, the mechanisms of action suggested in the specification (e.g., models for BMP signaling) are merely possible explanations for our observations while operation of the claimed invention is not necessarily dependent thereon.

All references, patent applications, and patents cited in this disclosure are hereby incorporated herein by reference in their entirety and indicate the high skill of artisans in this field. In particular, some of the results shown above were published by Xie and Spradling in Cell 94, 251–260 (1998) after the filing date of priority U.S. application Ser. No. 60/094,008.

REFERENCES

Allis et al. (1979) Develop. Biol. 69, 451–65.

Arora et al. (1995) Cell 81, 781–790.

Attisano and Wrana (1998) Curr. Opin. Cell Biol. 10, 188–194.

Baker et al. (1992) Genes Develop. 6, 2312–2326.

Beyers et al. (1987) J. Cell Biol. 105, 2103–2110.

Bitgood and McMahon (1995) Develop. Biol. 172, 126–138.

Brand and Perrimon (1993) Development 118, 401–415.

Brook and Cohen (1996) Science 273, 1373–1377.

Brummel et al. (1994) Cell 78, 251–261.

Burke and Basler (1996) Development 122, 2261–2269.

Burke et al. (1984) Somat. Cell. Mol. Genet. 10, 579–588.

Cadigan and Nusse (1997) Genes Develop. 11, 3286–3305.

Campbell and Tomlinson (1999) Cell 96, 553–562.

Capecchi (1989) Science 244, 1288–1292.

Chen and Baker (1996) Development 124, 205–218.

Das et al. (1998) Development 125, 1519–1528.

de Cuevas et al. (1997) Annu. Rev. Genet. 31, 405–428.

de Cuevas and Spradling (1998) Development 125, 2781–2789.

Doe and Spana (1995) Neuron 15, 991–995.

Forbes et al. (1996a) Development 122, 1125–1135.

Forbes et al. (1996b) Development 122, 3283–3294.

Forbes and Lehmann (1998) Development 125, 679–690.

Gateff and Mechler (1989) Crit. Rev. Oncogen. 1, 221–245.

Greider et al. (1995) Cell 81, 791–800.

Groppe et al. (1998) J. Biol. Chem. 273, 29052–29065.

Haerry et al. (1998) Development 125, 3977–3987.

Heldin et al. (1997) Nature 390, 465–471.

Hoffmann (1992) Mol. Reprod. Develop. 32, 173–178.

Hogan (1996a) Genes Develop. 10, 1580–1594.

Hogan (1996b) Curr. Opin. Genet. Develop. 6, 432–438.

Hudson et al. (1998) Development 125, 1407–1420.

Hursh et al. (1993) Development 117, 1211–1222.

Inoue et al. (1998) Mol. Biol. Cell 9, 2145–2156.

Jazwinska et al. (1999) Cell 96, 563–573.

Jiang and Struhl (1996) Cell 86, 401–409.

Johnson and Tabin (1995) Cell 81, 313–316.

Kawabata et al. (1998) Cytokine Growth Factor Rev. 9, 49–61.

Koller and Smithies (1992) Annu. Rev. Immunol. 10, 705–730.

Lagna et al. (1996) Nature 383, 832–836.

Lawrence and Struhl (1996) Cell 85, 951–961.

Lawson et al. (1999) Genes Develop. 13, 424–436.
Lecuit and Cohen (1997) Nature 388, 139–145.
Lee et al. (1994) Science 266, 1528–1537.
Lengyel et al. (1975) Meth. Cell Biol. 10, 195–208.
Letsou et al. (1995) Cell 80, 899–908.
Liang et al. (1994) Development 120, 12011211.
Lin (1997) Annu. Rev. Genet. 31, 455–491.
Lin et al. (1994) Development 120, 947–956.
Lin and Spradling (1997) Development 124, 2463–2476.
Manseau et al. (1997). Develop. Dynamics 209, 310–322.
Margolis and Spradling (1995) Development 121, 3797–3807.
Massague (1996) Cell 85, 947–950.
Matunis et al. (1997). Development 124, 4383–4391.
McKearin and Ohlstein (1995) Development 121, 2937–2947.
McKearin and Spradling (1990) Genes Develop. 4, 2242–2251.
Minami et al. (1999) Nature 398, 242–246.
Mishina et al. (1995) Genes Develop. 9, 3027–3037.
Morrison et al. (1997) Cell 88, 287–298.
Murata and Wharton (1995) Cell 80, 747–756.
Nellen et al. (1994) Cell 78, 225–237.
Nellen et al. (1996) Cell 85, 357–368.
Newfeld et al. (1997) Genetics 145, 297–309.
Ohlstein and McKearin (1997) Development 124, 3651–3662.
Okada et al. (1974) Develop. Biol. 39, 286–294.
Padgett (1999) Curr. Biol. 9, R408–411.
Padgett et al. (1987) Nature 325, 81–84.
Padgett et al. (1993) Proc. Natl. Acad. Sci. USA 90, 2905–2909.
Padgett et al. (1998) Bioessays 20, 382–390.
Panganiban et al. (1990) Mol. Cell. Biol. 10, 2669–2277.
Penton et al. (1994) Cell 78, 239–250.
Penton et al. (1997) Science 275, 203–206.
Perrimon (1995) Cell 80, 517–520.
Potter and Loeffler (1990) Development 110, 1001–1020.
Raftery and Sutherland (1999) Develop. Biol. 210, 251–268.
Ruberte et al. (1995) Cell 80, 889–897.
Schneider (1972) J. Embryol. Exp. Morphol. 27, 353–365.
Schoffteld, R. (1978) Blood Cells 4, 7–25.
Sekelsky et al. (1995) Genetics 139, 1347–1358.
Spradling et al. (1975) Meth. Cell Biol. 10, 185–194.
Spradling et al. (1995) Proc. Natl. Acad. Sci. USA 92, 10824–10830.
Spradling et al. (1997) Cold Spring Harbor Symp. Quant. Biol. 62, 25–34.
Tsuneizumi et al. (1997) Nature 389, 627–631.
Twombly et al. (1996) Development 122, 1555–1565.
Van Deusen (1977) J. Embryol. Exp. Morphol. 37, 173–185.
Wharton et al. (1996) Genetics 142, 493–505.
Wharton et al. (1999) Genetics 152, 629–640.
Wieschaus and Szabad (1979) Develop. Biol. 68, 29–46.
Winnier et al. (1995) Genes Develop. 9, 2105–2116.
Wisotzkey et al. (1998) Development 125, 1433–1445.
Xie et al. (1994) Science 263,1756–1759.
Xu and Rubin (1993) Development 117, 1223–1237.
Yamaji et al. (1994) Biochem. Biophys. Res. Commun. 205, 1944–1951.
Zacci and Lipshitz (1996) Zygote 4, 159–166.
Zhang and Spradling (1994) Proc. Natl. Acad. Sci. USA 91, 3539–3543.
Zhang and Bradley (1996) Development 122, 2977–2986.
Zhao et al. (1996) Genes Develop. 10, 1657–1669.
Zhao et al. (1998) Development 125, 1103–1112.

Standard procedures in the art are described in generally available references and laboratory manuals like Ausubel et al. (*Current Protocols in Molecular Biology*, Wiley, 1999); Birren et al. (*Genome Analysis Series*, CSHL, 1997–1999); Coligan et al. (*Current Protocols in Immunology*, Wiley, 1999); Coligan et al. (*Current Protocols in Protein Science*, Wiley, 1999); Diffenbach and Dveksler (*PCR Primer*, CSHL Press, 1995); Harlow and Lane (*Antibodies and Using Antibodies*, CSHL, 1988 and 1999); Hogan et al. (*Manipulating the Mouse Embryo*, CSHL, 1994); Janson and Ryder (*Protein Purification*, Wiley, 1997); Keller and Manak (*DNA Probes*, Stockton, 1993); Marshak et al. (*Strategies for Protein Purification and Characterization*, CSHL, 1996); Mullis et al. (*The Polymerase Chain Reaction*, Birkhauser, 1994); Murphy and Carter (*Trangenesis Techniques*, Humana, 1993); Pinkert, (*Trangenic Animal Technology*, Academic, 1994); Sambrook et al. (*Molecular Cloning*, CSHL, 1989); and Spector et al. (*Cells*, CSHL, 1998).

We claim:

1. A method for increasing the abundance of germline stem cells of Drosophila in vivo comprising:
    (a) providing a population comprising germilne stem cells in a female host transgenic Drosophila, wherein the transgenic Drosophila ectopically expresses Dpp wherein said ectopic expression of Dpp is in germanium cells using hs70-GAL4 and UAS-dpp; and
    (b) subjecting the germaria of the female host transgenic Drosophila to heat shock, wherein the heat shock stimulation increases the abundance of germline stem cells as compared to a population wherein the germaria of the female host transgenic Drosophila was not subjected to heat shock.

2. A method according to claim 1, wherein said germline stem cells are from an ovary.

3. A method according to claim 1 further comprising obtaining said germline stem cells from an embryo.

4. A method according to claim 1 further comprising maintaining at least one of said germline stem cells in a pluripotent state.

5. A method according to claim 1 further comprising maintaining at least one of said germline stem cells in a totipotent state.

6. A method according to claim 1 further comprising transferring at least one of said stimulated germline stem cells into a second host Drosophila.

7. A method according to claim 6, wherein at least one of said transferred germline stem cells is capable of contributing to two or more differentiated cell lineages of said second host Drosophila.

8. A method according to claim 6, wherein at least one of said transferred germline stem cells contributes to a germline cell lineage of said second host Drosophila.

9. A method according to claim 1 further comprising mutating at least one gene of said germline stem cell's genome.

10. A method according to claim 1 further comprising introducing one or more polynucleotides into said germline steam cell's genome.

11. A method according to claim 1 further comprising integrating a polynucleotide by homologous recombination at a targeted genetic locus of said germline stem cell.

12. A method according to claim 1 further comprising targeting at least one gene of said germline stem cell for homologous recombination selecting at least one germline stem cell which has undergone homologous recombination of said gene, and transferring said homologously recombined germline stem cells into another Drosophila such that said targeted gene is genetically transmitted through said another Drosophila's germline.

13. A method according to claim 1 further comprising isolating said increased abundance of germline stem cells and culturing said germline stern cells in vitro.

* * * * *